(12) United States Patent
Givens et al.

(10) Patent No.: US 6,426,622 B1
(45) Date of Patent: Jul. 30, 2002

(54) FIXTURE FOR EDDY CURRENT INSPECTION PROBES

(75) Inventors: Glenn D. Givens, Milford; James P. O'Connell, Fairfield; Joseph A. Traxler, Hamilton, all of OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/747,251

(22) Filed: Dec. 21, 2000

(51) Int. Cl.[7] .......................... G01R 33/00; G01N 27/90
(52) U.S. Cl. ...................... 324/262; 324/240; 324/261; 269/87.3; 269/254 CS
(58) Field of Search ................................ 324/240, 261, 324/262; 269/238, 254 CS, 87.3

(56) References Cited

U.S. PATENT DOCUMENTS

| | | | | |
|---|---|---|---|---|
| 2,893,275 A | * | 7/1959 | Lindemann | 269/254 CS |
| 3,626,358 A | * | 12/1971 | Klassen | 324/72.5 |
| 4,066,949 A | * | 1/1978 | Condrac | 324/262 |
| 4,638,602 A | * | 1/1987 | Cavalieri | 51/217 R |
| 4,644,274 A | * | 2/1987 | Casarcia | 324/262 |
| 4,757,258 A | * | 7/1988 | Kelly, Jr. et al. | 324/220 |
| 4,906,926 A | * | 3/1990 | Rogacki et al. | 324/236 |
| 4,986,771 A | * | 1/1991 | Braswell | 439/790 |
| 5,847,350 A | * | 12/1998 | Dorrel et al. | 219/69.15 |

* cited by examiner

*Primary Examiner*—Edward Lefkowitz
*Assistant Examiner*—Darrell Kinder
(74) *Attorney, Agent, or Firm*—V. G. Ramaswamy; Pierce Atwood

(57) ABSTRACT

A fixture for use with eddy current inspection probes facilitates inspection of airfoil leading and trailing edges. The fixture includes a fixture body having a hole formed in one side thereof for receiving a probe and a V-groove formed in another side thereof for receiving a workpiece surface. A clamp arm is pivotally mounted to the fixture body, and a spring is disposed between the clamp arm and the fixture body. The spring biases one end of the clamp arm towards the fixture body so that a workpiece can be clamped between the clamp arm and the fixture body.

19 Claims, 2 Drawing Sheets

FIXTURE FOR EDDY CURRENT INSPECTION PROBES

BACKGROUND OF THE INVENTION

This invention relates generally to eddy current inspection and more particularly to fixtures for facilitating the use of hand held eddy current inspection probes.

Eddy current inspection is a commonly used technique for nondestructively detecting discontinuities or flaws in the surface of items made of electrically conductive material, including many gas turbine engine components. Eddy current inspection techniques are based on the principle of electromagnetic. induction in which eddy currents are induced within the component under inspection by application of alternating magnetic fields. Known eddy current probes include absolute probes, which contain a single inductive coil, and differential probes, which have a drive coil and a sense coil. In the case of a differential probe, eddy currents are induced in the component under inspection when the probe is moved into proximity with the component by alternating magnetic fields created in the drive coil. The eddy currents produce a secondary magnetic field that is detected by the sense coil, which converts the secondary magnetic field into an electrical signal that may be recorded and/or displayed for analysis. As the eddy current probe is passed over the component, the presence of cracks and other discontinuities or deformations in the component will produce changes in the magnitude of the induced eddy current as compared to the magnitude of the induced eddy current in areas that do not have such anomalies. This results in corresponding variations in the magnitude of the signal output by the sense coil. Hence, the output signal, specifically the amplitude of the output signal variations, is an indication of the condition of the component. An eddy current machine operator may then detect and size flaws by monitoring and analyzing the output signals.

Rotor blades are used in the compressor and turbine sections of gas turbine engines for interacting with the gas stream flow of the engine. Rotor blades typically include a shank having a dovetail for mounting the blade to a rotor disk and an airfoil that extends radially outwardly from the shank and into the gas stream. The airfoil includes a pressure side and a suction side joined together at a leading edge and at a trailing edge. Rotor blades are ordinarily formed as a one-piece casting of a suitable superalloy, such as a nickel-based superalloy, which has acceptable strength at the elevated temperatures of operation in the gas turbine engine.

During engine operation, the leading and trailing can be susceptible fatigue cracking because of the high temperatures and pressures to which the blades are exposed. Furthermore, the trailing edges can experience cracking during the blade manufacturing process because they are very thin compared to the rest of the airfoil. Thus, it is common to frequently subject rotor blade leading and trailing edges to eddy current inspection before and after service.

This is typically accomplished with a hand held eddy current probe, wherein an operator moves the probe by hand along the leading or trailing edge of the rotor blade airfoil. However, this can often be a difficult procedure to perform because of probe normalization and "lift-off" variables. In other words, it is difficult for a human operator to maintain the probe at the proper angle and in constant contact while moving the probe over the surface being inspected. If either probe angle is altered or lift-off occurs, then the inspection integrity can become compromised. Accordingly, it would be desirable to have a means for maintaining probe angle and contact during eddy current inspections.

BRIEF SUMMARY OF THE INVENTION

The above-mentioned need is met by the present invention, which provides a fixture for use with eddy current inspection probes. The fixture includes a fixture body having a hole formed in one side thereof for receiving a probe and a V-groove formed in another side thereof for receiving a workpiece surface. A clamp arm is pivotally mounted to the fixture body, and a spring is disposed between the clamp arm and the fixture body. The spring biases one end of the clamp arm towards the fixture body so that a workpiece can be clamped between the clamp arm and the fixture body.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
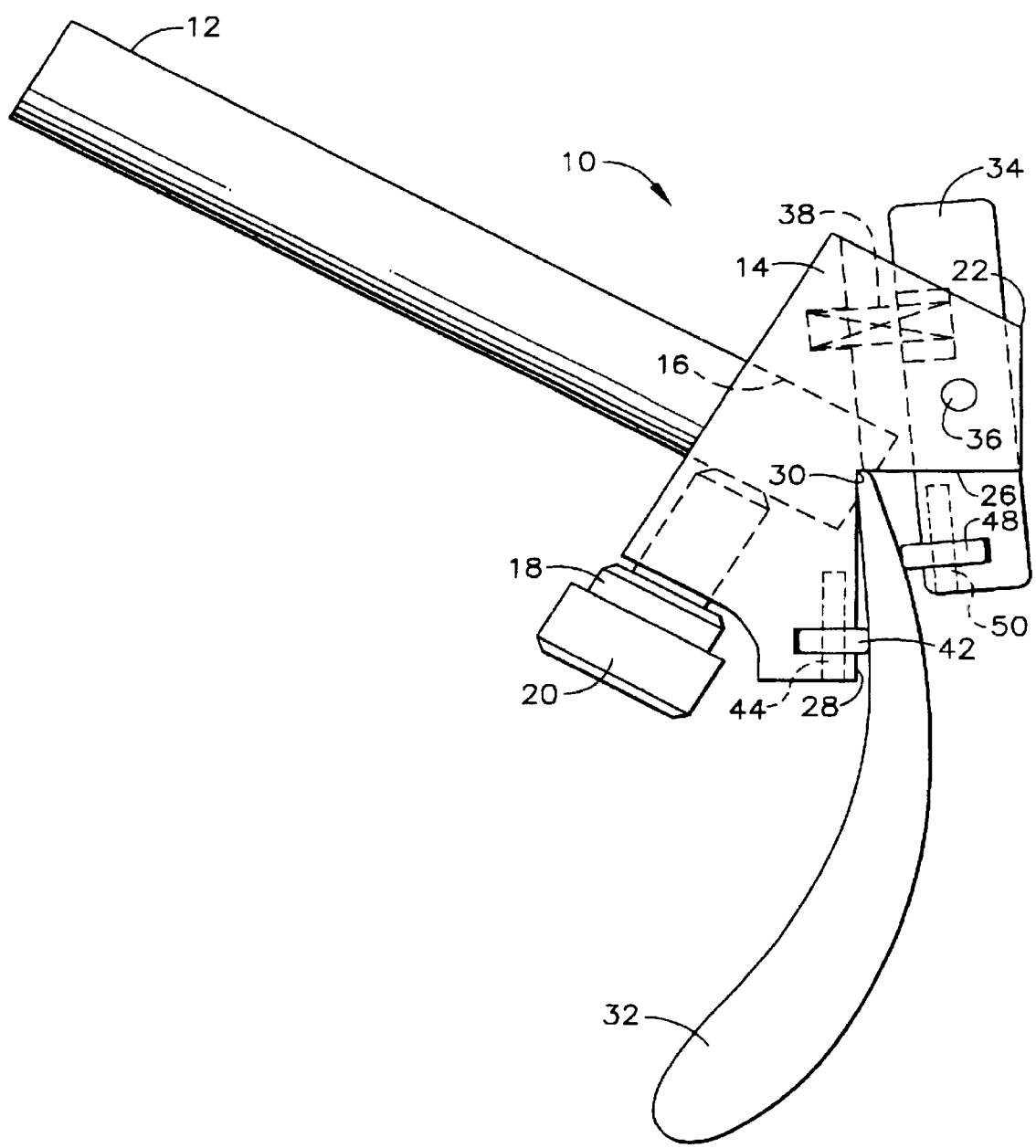
FIG. 1 is a top view of a fixture for an eddy current inspection probe in use with a rotor blade.
Figure 2:
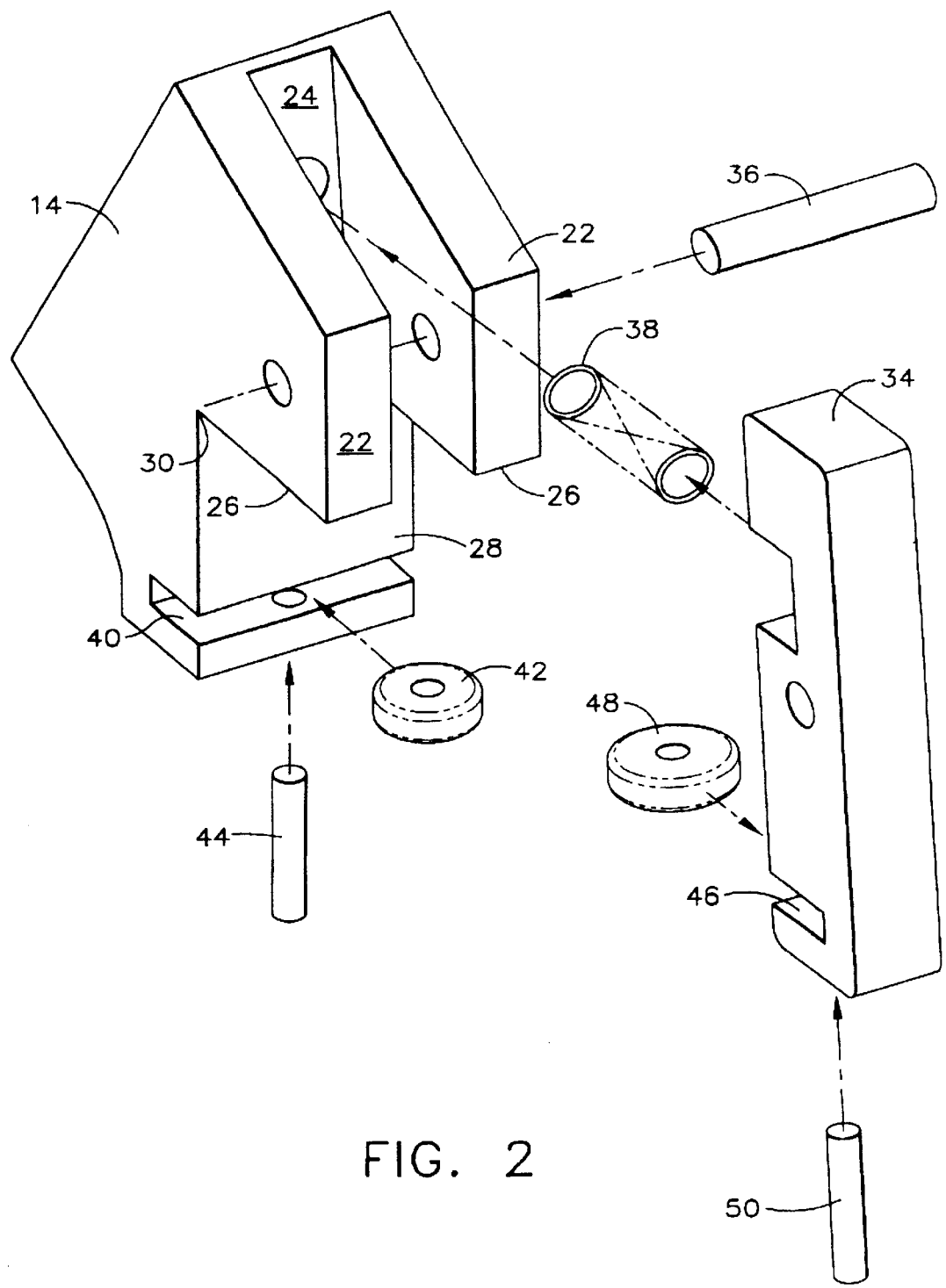
FIG. 2 is an exploded perspective view of the inspection fixture of FIG. 1.

Referring to the drawings wherein identical reference numerals denote the same elements throughout the various views, FIGS. 1 and 2 show an inspection fixture 10 that facilitates the inspection of the leading or trailing edge of an airfoil with a hand held eddy current probe 12. It is noted that while the Figures depict one preferred embodiment of the inspection fixture 10, it can be designed to accommodate a wide variety of eddy current probes.

The inspection fixture 10 comprises a fixture body 14 of a generally rectangular block shape having four sides and two ends. A hole 16 for receiving the eddy current probe 12 is formed in a first side of the fixture body 14, about midway between the two ends thereof. The hole 16 extends perpendicularly from the first side of the fixture body 14 to a second side, opposite to the first side. A set screw 18 is threaded into the fixture body 14 at a first end thereof. The set screw 18 extends perpendicularly to the probe hole 16 so as to engage the probe 12. Thus, tightening the set screw 18 against the probe 12 will retain the probe 12 in the hole 16. Loosening the set screw 18 will allow the probe 12 to be removed. A knurled knob 20 is provided to facilitate tightening and loosening of the set screw 18.

A pair of flanges 22 extend outwardly from the second side of the fixture body 14, adjacent to the second end thereof (i.e., the end opposite the set screw 18). The flanges 22 are spaced apart in a yoke configuration to define a channel 24 therebetween. Each flange 22 forms a planar edge 26 on the side closest to the first end of the fixture body 14. These edges 26 define a first planar surface of the fixture body 14. The fixture body 14 also includes a second planar surface 28 formed on the second side thereof, adjacent to the first end. The first and second planar surfaces 26, 28 intersect to define a V-groove 30 for receiving an airfoil edge of a blade 32 to be inspected. As shown in FIG. 1, the trailing edge of the blade 32 is being inspected; however, the inspection fixture could also be configured to be inspect the leading edge.

The V-groove 30 is aligned with the probe hole 16 so that the probe 12 is properly positioned with respect to the blade edge when the blade edge is received in the V-groove 30. The second planar surface 28 is oriented at a predetermined angle with respect to the central axis of the probe hole 16 (and thus with respect to the longitudinal axis of the probe 12). As will be explained below, this angle determines the orientation of the probe 12 when the blade edge is received in the V-groove 30.

A clamp arm 34 is disposed in the channel 24 between the two flanges 22. The clamp arm 34 is pivotally mounted to the fixture body 14 by a pivot pin 36 that extends between the two flanges 22 and through the clamp arm 34 at a point approximately midway between the two ends thereof. The clamp arm 34 is a relatively long, narrow member having a first end that extends beyond the flange edges 26 and a second end that extends beyond the second end of the fixture body 14. A spring 38 disposed in the channel 24 extends between the fixture body 14 and the clamp arm 34 for biasing the clamp arm 34. Specifically, the spring 38 engages the clamp arm 34 between its second end and the pivot pin 36 so as to bias the clamp arm first end towards the second planar surface 28 on the fixture body 14. Inward manual pressure exerted on the second end of the clamp arm 34 will pivot the clamp arm 34 against the spring pressure and widen the gap between the second planar surface 28 and the first end of the clamp arm 34.

A slot 40 is formed in the second planar surface 28, near the first end of the fixture body 14. A first guide wheel 42 is mounted in the slot 40 for rotation about a first axle 44. Another slot 46 is formed in the clamp arm 34, near the first end thereof. A second guide wheel 48 is mounted in the second slot 46 for rotation about a second axle 50. Thus, when the inspection fixture 10 is. mounted on the blade 32, the first guide wheel 42 contacts a first side (either the suction or pressure side) of the blade 32, and the second guide wheel 48 contacts the other side of the blade 32. The two axles 44, 50 are disposed in a common plane. More specifically, the axles 44, 50 are both perpendicular to the blade edge when the inspection fixture 10 is mounted on the blade 32. Thus, the guide wheels 42, 48 will smoothly guide the fixture 10 and probe 12 along the blade 32 while the blade edge is being scanned. Furthermore, the fixture body 14 is preferably, but not necessarily, made. of a self-lubricating plastic material such as the material sold under the trademark DELRIN®, to avoid metal-to-metal contact with the blade 32 during inspections.

In operation, the eddy current probe 12 is first placed in the probe hole 16 and secured with the set screw 18. The probe 12 is positioned in the hole 16 so that its end is aligned with the V-groove 30 situated at the end of the hole 16. Many commercially available hand held eddy current probes are provided with a notch in the end for engaging the surface to be inspected. In this case, the probe would be positioned in the hole 16 so that the probe notch was aligned with the V-groove 30.

Once the probe 12 is properly set in the fixture 10, the second end of the clamp arm 34 is pressed toward the fixture body 14 to open a gap between the first and second guide wheels 42, 48. The fixture 10 is then placed on the blade 32 so that the blade edge to be inspected is situated in the V-groove 30 and the first guide wheel 42 contacts a first side of the blade 32. In this position, the probe 12 will be properly oriented with respect to the blade edge because of the predetermined angle between the second planar surface 28 and the central axis of the probe hole 16. The clamp arm 34 is then released so that. the spring 38 will bias the clamp arm 34 toward with the blade 32 such that the second guide wheel 48 contacts the opposite side of the blade 32. The blade 32 is thus clamped between the first and second guide wheels 42, 48. At this point, the probe end will be in contact with the blade edge and oriented at the proper angle thereto. The inspection fixture 10 can then be moved by hand spanwise over the length of the blade edge with the guide wheels 42, 48 rolling over the respective blade airfoil surfaces. With this arrangement, an operator can easily maintain the probe 12 against the blade edge and with the proper orientation over the entire scan length. The inspection fixture 10 provides complete and repeatable coverage of airfoil edges and assures inspection integrity by minimizing operator dependency and reducing lift-off variables.

The inspection fixture 10 can be used to inspection either the leading or trailing edges of rotor blade airfoils, although the geometry may vary from application. That is, fixtures used for inspecting leading edges may require a different fixture geometry (particularly the angle of the second planar surface 28 with respect to the probe axis and the distance between first guide wheel 42 and the V-groove 30) than fixtures used for inspecting trailing edges. Furthermore, the inspection fixture 10 is not limited to use with rotor blades; it can also be used in the inspection of the leading and trailing edges of other types of airfoils, such as stator vanes.

The foregoing has described a spring loaded, wheel guided fixture for eddy current probes that targets a predetermined inspection zone with minimal variation. While specific embodiments of the present invention have been described, it will be apparent to those skilled in the art that various modifications thereto can be made without departing from the spirit and scope of the invention as defined in the appended claims.

What is claimed is:

1. A fixture for use with an eddy current inspection probe, said fixture comprising:
   a fixture body having a hole formed therein for receiving said probe, said fixture body including means for aligning a workpiece with said hole; and
   a clamp arm pivotally mounted to said fixture body, said clamp arm being spring-biased for clamping said between said clamp arm and said fixture body.

2. The fixture of claim 1 further comprising a first guide wheel rotatively mounted to said fixture body, and a second guide wheel rotatively mounted to said clamp arm.

3. The fixture of claim 2 wherein said first and second guide wheels have axes of rotation that are substantially parallel to one another.

4. The fixture of claim 1 wherein said means for aligning said workpiece with said hole comprise a V-groove formed in said fixture body.

5. The fixture of claim 4 wherein said V-groove is defined by intersecting planar surfaces formed on said fixture body.

6. The fixture of claim 5 wherein said hole defines a central axis and a first one of said planar surfaces is oriented at a predetermined angle with respect to said central axis.

7. The fixture of claim 6 further comprising a first guide wheel rotatively mounted to said first planar surface, and a second guide wheel rotatively mounted to said clamp arm.

8. The fixture of claim 1 wherein said fixture body includes a pair of flanges extending outwardly from one side thereof, and said clamp arm is pivotally mounted to said fixture body between said flanges.

9. The fixture of claim 8 further comprising a pivot pin extending between said flanges and through said clamp arm.

10. The fixture of claim 1 further comprising a set screw threaded into said fixture body for engaging said probe.

11. A fixture for use with an eddy current inspection probe, said fixture comprising:
- a fixture body having a hole formed in one side thereof for receiving said probe and a V-groove formed in another side thereof for receiving a workpiece surface, said V-groove being aligned with said hole;
- a clamp arm pivotally mounted to said fixture body, said clamp arm having first and second ends; and
- a spring disposed between said second end of said clamp arm and said fixture body for biasing said first end of said clamp arm towards said fixture body.

12. The fixture of claim 11 further comprising a first guide wheel rotatively mounted to said fixture body, and a second guide wheel rotatively mounted to said first end of said clamp arm.

13. The fixture of claim 12 wherein said first and second guide wheels have axes of rotation that are substantially parallel to one another.

14. The fixture of claim 11 wherein said V-groove is defined by intersecting planar surfaces formed on said fixture body.

15. The fixture of claim 14 wherein said hole defines a central axis and a first one of said planar surfaces is oriented at a predetermined angle with respect to said central axis.

16. The fixture of claim 15 further comprising a first guide wheel rotatively mounted to said first planar surface, and a second guide wheel rotatively mounted to said first end of said clamp arm.

17. The fixture of claim 11 wherein said fixture body includes a pair of flanges extending outwardly from one side thereof, and said clamp arm is pivotally mounted to said fixture body between said flanges.

18. The fixture of claim 17 further comprising a pivot pin extending between said flanges and through said clamp arm.

19. The fixture of claim 11 further comprising a set screw threaded into said fixture body for engaging said probe.

* * * * *